United States Patent [19]

Gisser et al.

[11] Patent Number: 5,272,624
[45] Date of Patent: Dec. 21, 1993

[54] CURRENT PATTERNS FOR IMPEDANCE TOMOGRAPHY

[75] Inventors: David G. Gisser, Albany; Jonathan C. Newell, Glenmont; David Isaacson, Latham; John C. Goble, West Berne, all of N.Y.

[73] Assignee: Rensselaer Polytechnic Institute, Troy, N.Y.

[21] Appl. No.: 591,615

[22] Filed: Oct. 2, 1990

[51] Int. Cl.⁵ ............................................. G06F 15/42
[52] U.S. Cl. ............................ 364/413.013; 128/734
[58] Field of Search ................... 364/413.13, 413.15, 364/413.02; 128/734

[56] References Cited

U.S. PATENT DOCUMENTS

| | | | |
|---|---|---|---|
| 4,486,835 | 12/1984 | Bai et al. | 364/413.13 |
| 4,539,640 | 9/1985 | Fry et al. | 364/413.13 |
| 4,649,932 | 3/1987 | Smith | 128/734 |
| 4,920,490 | 4/1990 | Isaacson | 364/413.13 |

FOREIGN PATENT DOCUMENTS 2138148 10/1984 United Kingdom .

OTHER PUBLICATIONS

"An Electric Current Tomograph", Newell et al., IEEE Trans of Biomed. E., vol. 35, No. 10, Oct. 1988.

Primary Examiner—Robert A. Weinhardt
Attorney, Agent, or Firm—Notaro & Michalos

[57] ABSTRACT

In an electrical impedance imaging system that is capable of forming images based on internal resistivity of a body, an array of electrodes is applied to the surface of the body and energized by a plurality of current generators. Each current generator is controlled to produce current patterns containing single fixed magnitudes. The current generators are also controlled to apply current to the respective electrode only when the current generator is at peak current value to minimize transient conditions and maximize the rate at which images can be produced.

5 Claims, 6 Drawing Sheets

System Block Diagram

FIG. 3 System Block Diagram

FIG. 4
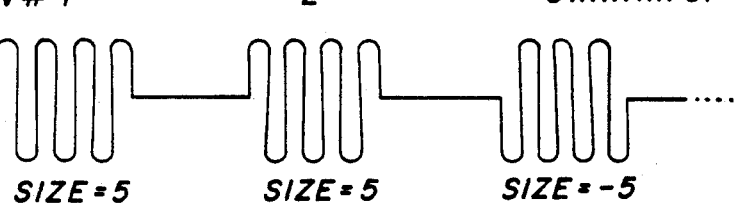
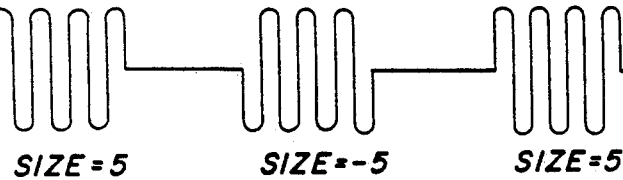
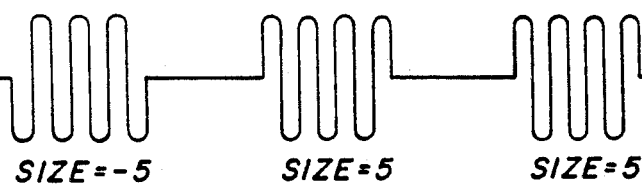

CURRENT PATTERNS FOR IMPEDANCE TOMOGRAPHY

STATEMENT OF GOVERNMENT INTEREST

This invention was made in part with Government support under National Science Foundation Grant No. EET-8706340 and National Institutes of Health Grants No. GM-39388 and GM-42935. The Government has certain rights in this invention.

FIELD AND BACKGROUND OF THE INVENTION

The present invention relates in general to impedance tomography, and in particular to a new and useful method and apparatus for the simplified generation of current patterns for use in electric current computed tomography (ECCT) which includes synchronization for eliminating transients in switched RC coupled circuits used to practice the invention.

An apparatus for practicing electric current tomography comprising 32 electrodes and a plurality of current generators is disclosed in an article by Newell, Gisser and Isaacson entitled "An Electric Current Tomograph", IEEE TRANSACTIONS ON BIOMEDICAL ENGINEERING, Vol. 35, No. 10, October 1988.

A process and apparatus for utilizing a similar array of electrodes in computed tomography is disclosed in U.S. Pat. No. 4,920,490 granted to one of the co-inventors of the present application on Apr. 24, 1990. U.S. Pat. No. 4,920,490 and the subject matter therein is assigned to and owned by the assignee and the owner of the invention defined herein at the time the invention defined herein was made. The invention defined herein was made before the date U.S. Pat. No. 4,920,490 was granted.

UK Patent GB 2,138,148 to Smith published Jul. 30, 1986 discloses another apparatus and method of measuring impedances in a zone of the body, which utilizes a large number of electrodes placed in contact with the body, to which currents are applied. Potential differences are then derived which result from the currents through various zones of the body. These potential differences are representative of the impedance of these zones.

Walsh functions are a special set of mathematical functions first described in 1923. One of the special characteristics of a Walsh function is that it only has two values, either $-1$, or $+1$. These two values are conveniently converted to the two binary states of zero (0) and one (1). Unlike Fourier analysis which is based on sets of sine and cosine functions, analysis using Walsh functions is based on sets of square waves, which at any point in time, may only have a value of $+1$ or $-1$. The characteristics of Walsh functions are well known in the literature and these characteristics are advantageously used in the present invention.

SUMMARY OF THE INVENTION

The present invention involves the use of a simplified method for producing a useful current pattern in impedance tomography and a synchronization method for eliminating transients therein. The simplified current pattern technique for impedance imaging uses an apparatus which is simpler than the full 32-electrode, variable amplitude system now used. It is of intermediate complexity between the one-generator fixed-sized devices of others, and the 32-generator variable-sized device of U.S. Pat. No. 4,920,490. The invention uses a multi-generator fixed-size device. Images reconstructed from such a device are at least in some cases of interest, of comparable quality to the images made by the more complex device. In general, the technique of the invention constitutes an improvement in the overall image-making scheme. This will be true particularly if the simplified patterns can be made adaptive, and generate pictures of comparable quality to the full system.

The invention also includes a system for eliminating a problem which occurs in impedance imaging on living subjects who are studied by high-speed machines. A high-speed current tomograph changes its current patterns frequently, and each change may be accompanied by a transient which must be allowed to decay before meaningful data can be collected. If the instrument is properly synchronized, this transient is not produced, and therefore the instrument can run much faster. The innovation of the invention is two-fold: first that the problem exists at all, and second the solution of that problem once it is recognized. This disclosure may be seen as an important improvement in the technique of U.S. Pat. No. 4,920,490.

The field of the invention is in electrical impedance imaging which uses means for forming images of the internal resistivity of a body based on measurements of voltage and current at its surface. Another improvement of the invention is in the use of currents of a single fixed magnitude, rather than variable current amplitudes.

The invention permits the use of simplified current generators and simplified control of these generators. Present technology for impedance imaging contemplates continuously variable current amplitudes, with the resulting need for computer control of a complex circuit. Great simplification is obtained when only one amplitude is required.

This simplification of current patterns results in a theoretical degradation of available information. The practical effect of this degradation is minimal or zero for simple images, and unknown for more complex images.

Accordingly, one object of the present invention is to provide, in an electrical impedance imaging system having means for forming images of internal resistivity of a body using an array of electrodes on the surface of the body, a plurality of current generators, one for applying a current waveform to each electrode, and means for measuring a voltage at the surface of the body near or at each electrode, the improvement comprising: controlling each current generator to apply a series of fixed magnitude current values or waveforms to each electrode; and measuring the voltage at the surface of the body at or near each electrode to form an image.

A further object of the present invention is to control each current generator so that each current produced by each generator is an ac current having either direct or inverse polarity but the same value, the method including initially applying all currents to their respective electrodes at the instant when the ac current waveform is at a peak current value.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

BRIEF DESCRIPTION OF THE DRAWINGS

In the drawings:

FIG. 4 is a composite diagram showing the timing and relationship between a plurality of Walsh function current patterns to be applied to the electrodes of the apparatus in FIG. 3;

DESCRIPTION OF THE PREFERRED EMBODIMENT

Figure 1:
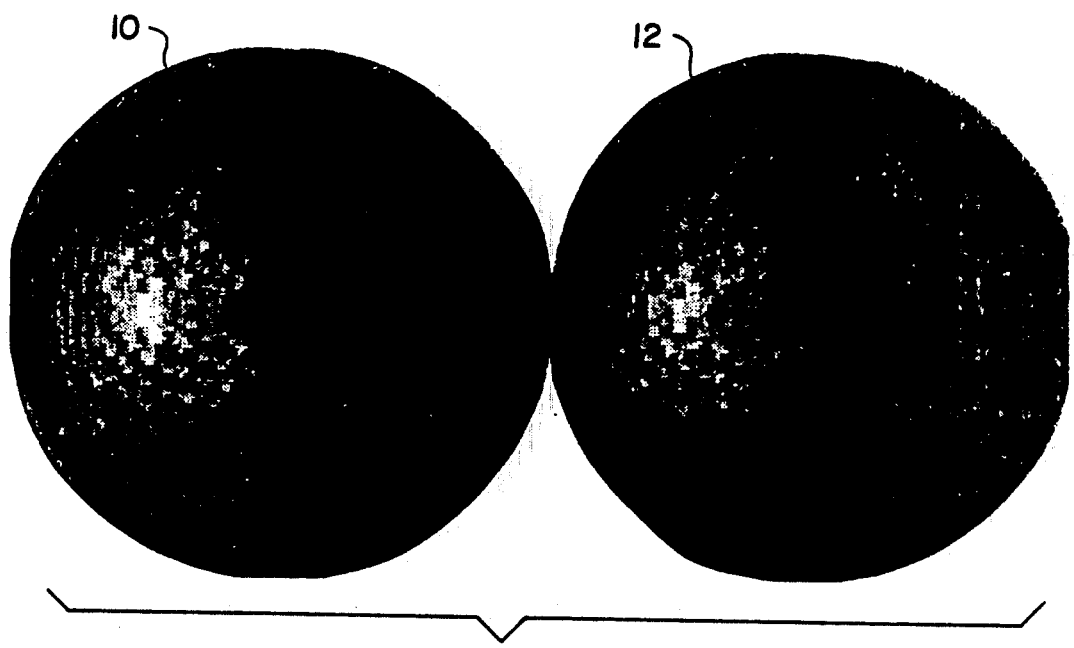
FIG. 1 illustrates a side by side pair of computer generated images, one utilizing the variable current patterns of U.S. Pat. No. 4,920,490, and the other utilizing the simplified current patterns of the present invention.

The effect for a simple image is shown in FIG. 1, which compares two images, one obtained by the full continuously variable currents at 10 and the second obtained by single-level currents of the invention at 12. These images are indistinguishable.

Figure 2:
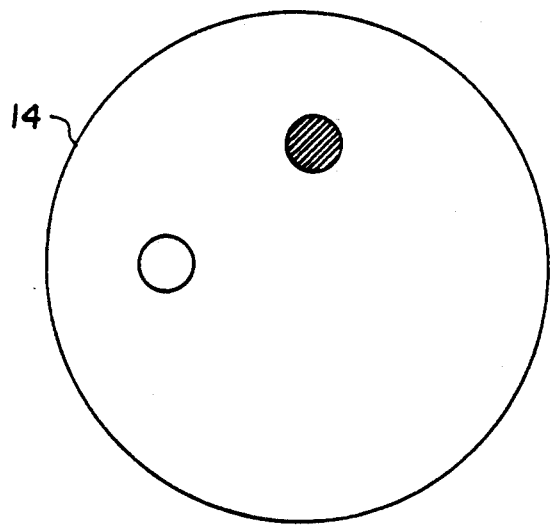
FIG. 2 is a schematic illustration of the actual target utilized for generating the images of FIG. 1.

FIG. 2 show the actual target from which FIG. 1 was formed.

Walsh functions are known in the literature as noted above. The application of Walsh techniques to impedance imaging, and the satisfactory result for image formation is a novel part of the present invention.

The Walsh function type current patterns are an improvement that does not necessarily improve the speed but rather the simplicity of the invention over earlier techniques. An impedance (or admittance) tomography system is one in which patterns of currents are applied through a set of electrodes to the surface of the object under test. The voltages at the electrodes are measured and this information, along with knowledge of the external geometry of the object, can be used to calculate values of resistivity at each of a large number of interior points of the object.

A map of a set of such points in a particular plane with resistivity variations shown as shades of gray, or color variations, is often called a tomographic cross-sectional impedance image. Specific impedance is defined as the impedance between opposite faces of a solid cube of material whose dimensions are $1 \times 1 \times 1$ cm, such impedance comprising both real and reactive components. In the present invention, two kinds of impedance images are made, one showing variations of the real, or resistive component of the impedance, and the other showing quadrature, or reactive components.

Such an impedance tomography system can be used to detect cracks or other flaws in solids, and impedance inhomogeneities in solids or liquids. There are also a number of medical applications where the object under test is a portion of the body, such as a limb or portion of the thorax or abdomen. This disclosure is limited to such medical applications, although industrial uses may also be of importance and may use the present invention.

Figure 7:
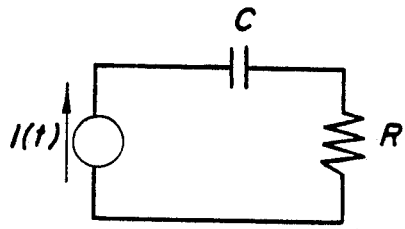
FIG. 7 is a simplified equivalent circuit to the circuit of FIG. 6.

Design constraints for medical applications are more stringent than for other applications for several reasons. One is that people can feel "electric shock" when current flow through the skin exceeds a certain threshold value. This threshold of perception is at much higher current values when the frequency of the current used is relatively high. Medical tomographic systems therefore use relatively high ac frequencies, and also use blocking capacitors to prevent dc currents from flowing either in the electrodes or the patient. An example is capacitor 101 in FIGS. 7 and 8.

Another problem is that for many organ systems the impedance is not constant, but varies with respiration or cardiac cycle or both. Any system that makes its needed sets of measurements over a relatively long period of time therefore smears these temporal impedance variations, much as an optical camera with a long exposure time smears images of moving objects. The present invention is a system that is capable of making its complete set of measurements in a small fraction of a cardiac cycle.

Figure 3:
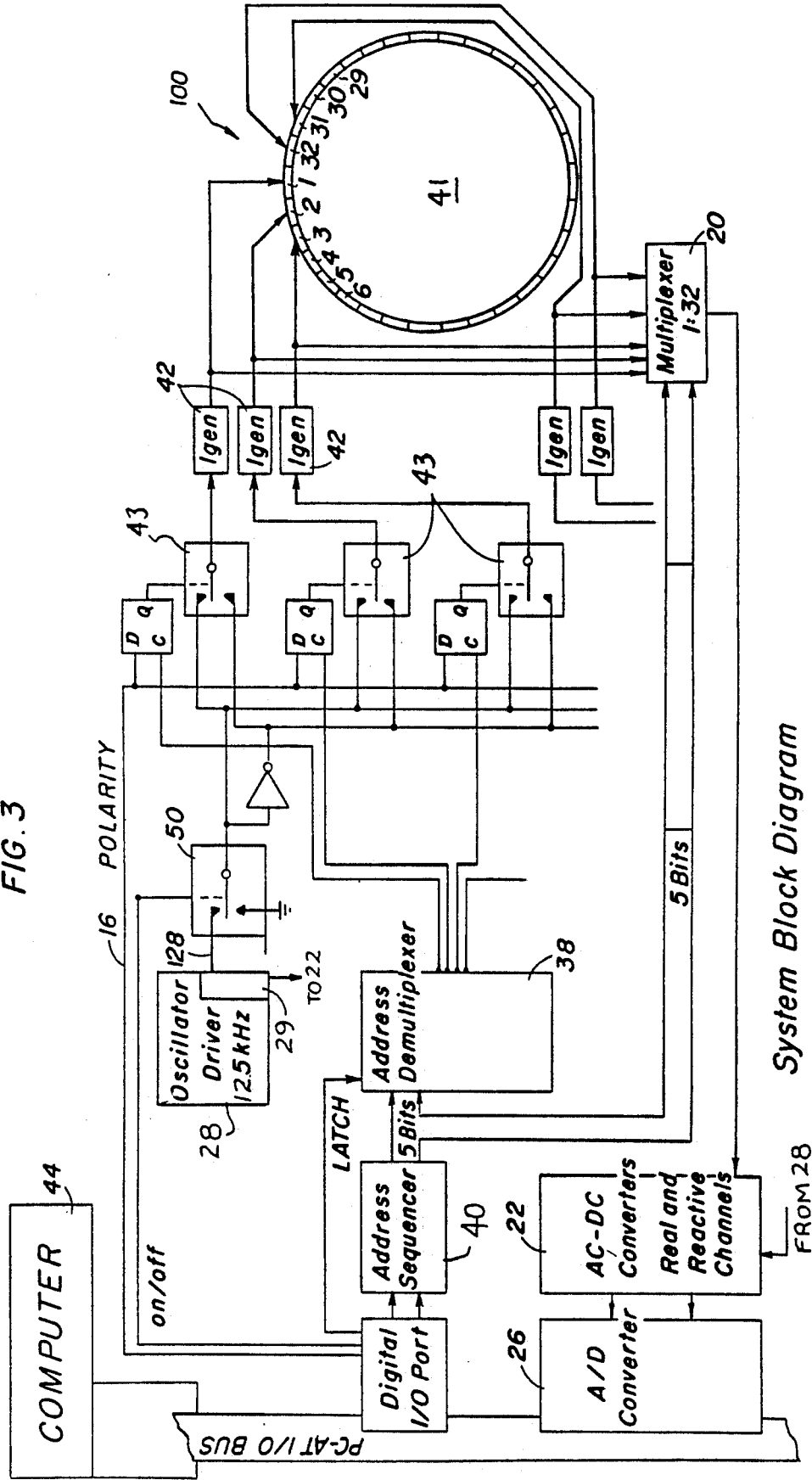
FIG. 3 is a block diagram showing an apparatus which can be used to produce images according to the present invention.

The nature of the problem to be solved by the invention can be understood by taking for example, a two-dimensional system with 32 electrodes uniformly distributed in an array 100, in one plane 34 around the periphery of a body part 41 as shown in FIG. 3. A set of 32 currents is applied, half positive and half negative, and distributed in a sinusoidal fashion, and then the voltage at every electrode is measured. The currents are then changed to new values which make two full sinusoidal variations as one proceeds along the 32 electrodes. The voltages are again measured, and then a third set of currents is applied which make three spatial sinusoids, and the voltages measured again. This process continues until a total of 31 different current patterns have been applied and 62 sets of 32 voltages per set have been measured. The number of voltage readings is doubled to accommodate up to 62 readings if both real and reactive components are measured. Needless to say, there are many technical problems associated with such a procedure if the total time available is limited to a fraction of a second.

The ac currents supplied to the electrodes originate in an oscillator 28, which must be on continually to ensure its stability. The buffered oscillator output is then applied to a polarity switch 43 which determines its polarity according to information from a controlling computer 44. The voltage signal is then changed to a current signal of appropriate polarity by an appropriate current generator circuit 42 and routed to an electrode. This is done for each electrode separately. In such a system, when setting up a current pattern, the digital information for each polarity switch 43 arrives at the switch sequentially, so new polarities of current are applied first to the first electrode, then to the second, and so on.

When done in this manner, there is a problem. Although the individual electrodes inject high frequency current, during the turn-on process a number of electrodes may first turn on and inject current of one polarity. At some later time others of opposite polarity turn on. The result is a transient effective current variation whose period approximates the set-up time rather than the much shorter period of the ac oscillator. This slower transient may be perceptible to a human subject, and should therefore be avoided.

Effective avoidance measures according to this invention involve either energizing all of the polarity switches simultaneously or using an analog switch schematically shown at 50 in FIG. 3 to suddenly connect the oscillator to the polarity switches after they have all been digitally set.

There is another important reason for applying signals to all of the electrodes of the system at a particular time. The time chosen should be carefully synchronized with the oscillator signal so that it occurs at the positive or negative peak of the current wave form. If this is not done, then any series capacitance will develop a voltage across it proportional to the integral of the current. If, as is often the case, the internal resistance of the current source is low at frequencies approaching zero, there is then a transient period during which the load voltage contains both the proper oscillator frequency and additionally a dc signal due to integration of the first part of the ac, which slowly dies out. The measurement of the ac voltage must be made quickly, and the extra time required to wait until the transient dies out is not needed if switching is done at the peak of the current cycle. It is useful to note that this remedy is appropriate not only for the usual dc blocking capacitance, but also for any capacitances associated with the electrodes and with the subject's tissues, especially the skin.

The invention thus provides a multi-electrode impedance tomography system in which each electrode has a separately controllable ac current source, and in which the voltage measurements on the electrodes must be made speedily, the invention including an energizing switch that is synchronized to close at the peak value of the current waveform (or at the center of the positive or negative waveform part if a square wave is used) in order to avoid inducing transients.

The overall system architecture of FIG. 3 is based on FIG. 4 of U.S. Pat. No. 4,920,490 and is designed for maximum flexibility with a minimum of special-purpose hardware. The system of U.S. Pat. No. 4,920,490 is an array of thirty-two current generators each of which has a separately programmable output level. A single voltmeter is attached sequentially through a multiplexer to each electrode of an array in a tank for measurement purposes. This special-purpose hardware is connected to the microcomputer (e.g. an IBM PC-AT) through a general-purpose analogue and digital interface board (e.g., a Data Translation DT2800). Synchronization between the instrument and software is accomplished by having the software write clock signals to a digital output port. A stable sinusoidal oscillator, at 12.5 kHz is included in the instrument. FIG. 3 of the present invention also uses an array of 32 electrodes 100.

Figure 6:
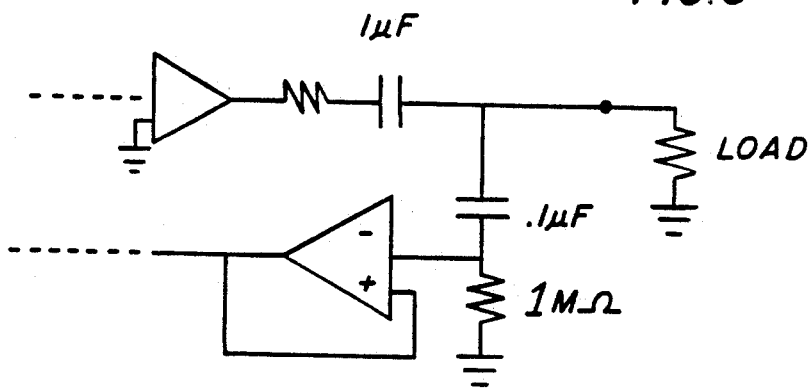
FIG. 6 is a schematic diagram of a circuit which can be utilized as a current source according to the present invention.

The current generators of the invention are of simplified type shown in FIG. 6. The output current has only two discrete values as shown in FIG. 4.

The digital multiplexer 20 selects one of the 32 electrodes and connects it to the input stage of the voltmeter 22. This meter consists of a synchronous full-wave demodulator (AD 630). The demodulator is an active switching device synchronized with the oscillator output through an adjustable phase shifter, which compensates for small phase shifts elsewhere in the circuit.

The detector switches at the exact zero crossings of the real component of the voltage signal.

This voltage is sampled by the analogue-to-digital convertor (ADC) 26 of the interface board (DT 2801/5716), which has 16 bit resolution, programmable gain, and is under software control.

A single digital sequencer 40 addresses both the current generators and the demultiplexer 20 for the voltmeter 22. Under software control, a master reset signal assures that the sequence begins with channel 1. Sequential counters 38 are then used to address the polarity switches 43. While the digital value representing the desired polarity for each current generator is present, a latching signal locks the switch in that position. When the switch addressing lines 16 is enabled, new current-specifying words are latched into the switches, so that new currents are applied to each electrode which may be all of the same amplitude as in FIG 4, or of different amplitudes as in FIG 5. During the read sequence, when the software does not enable the switch address line 16, the counter addresses each channel of the multiplexer 20 in sequence and presents the output of each electrode to the voltmeter 22. The ADC 26 input is then read by the software as the desired input data.

The switch 50 in FIG. 3 is normally connected in the condition that applies zero volts to all current sources. An oscillator output drives several auxiliary circuits 29. One of these detects the zero crossing points and uses them to generate a signal to drive the synchronous demodulator in the voltmeter 22. Another produces a phase shifted signal that can be adjusted for exactly ninety degrees. This one also has its zero crossings detected. They are at the positive and negative peaks of the current signals. They are also used for the demodulator when reactive voltage measurements are required.

When the computer sequence calls for a set of voltage measurements, it asserts a digital signal line high. At the next positive peak of the current waveform, the switch 50 is closed, and all electrodes are fed currents for a finite number of full cycles of the oscillator over line 128 during which time all 32 electrode voltages are measured. The switch output is then again connected to zero (ground) until after the next current pattern is ready to be applied.

FIG. 4 illustrates one pattern which exclusively uses ac currents of 5 and −5 mA. 31 current patterns are produced which are applied in sequence to each of the electrodes. 31 current patterns are produced by the 32 current generators for servicing all of the electrodes in FIG. 1. According to the present invention, it has been found that the very simplified ac current patterns which either have the value +5 mA or −5 mA still produce images of high resolution as demonstrated in FIG. 1.

Figure 5:
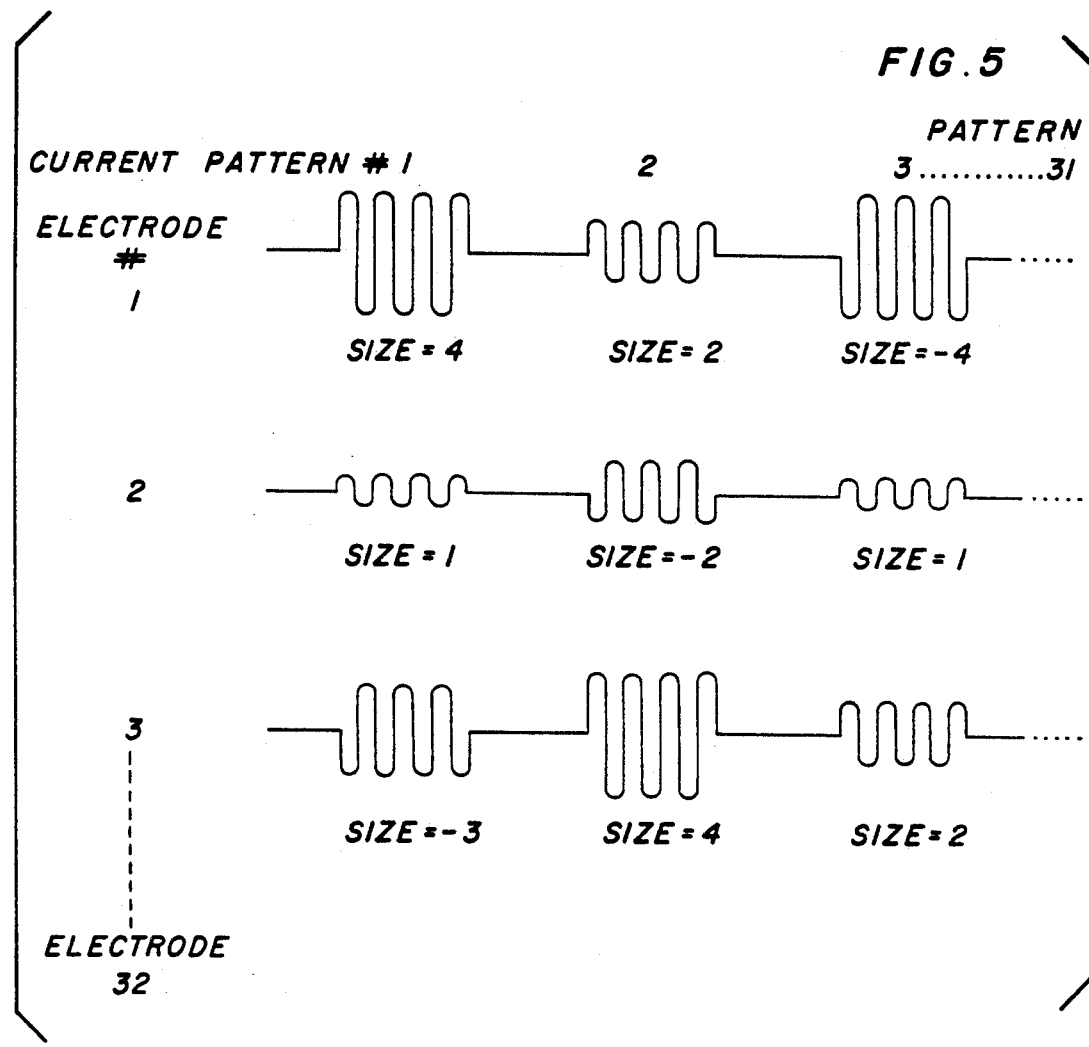
FIG. 5 is a view similar to FIG. 4 showing other well known patterns which can be utilized in accordance with the present invention.

FIG. 5 shows another example of the present invention which utilizes patterns of variable magnitudes with different magnitudes used in each pattern of the sequence of patterns applied to the electrodes. Here the pattern amplitudes illustrated are positive or negative and have amplitudes such as 1, 2, 3, or 4 mA.

By utilizing Walsh functions, the inventors have been able to greatly simplify the character of the current patterns by use of patterns such as FIG. 4 instead of FIG. 5, without any appreciable loss in image quality.

In conjunction with applying the discrete value current patterns to the electrodes, voltages at the electrodes are also read in a sequential pattern by the apparatus of FIG. 3. In order to allow for faster operation, the inventors consider the system dynamics involved with the setting up of digital input to the attenuaters and considered the question of how soon after the set up can sampling of the electrode voltage take place.

In the apparatus of FIG. 3, the oscillator 28 operates continuously. Similarly, the polarity switches are known to have a phase shift which is less than a degree at 12 kHz and having no low frequency limits.

The only source of difficulty postulated by the inventors were the current generators.

Figure 8:
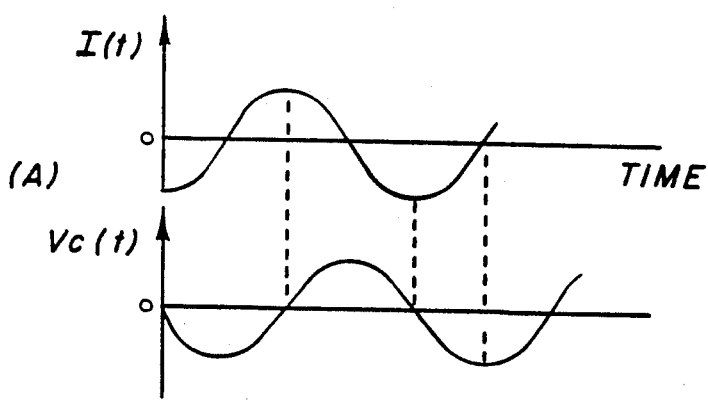
FIG. 8 is a composite graph plotting current and voltage against time to illustrate the first few cycles which are produced by the circuit of FIGS. 6 and 7.
Figure 9:
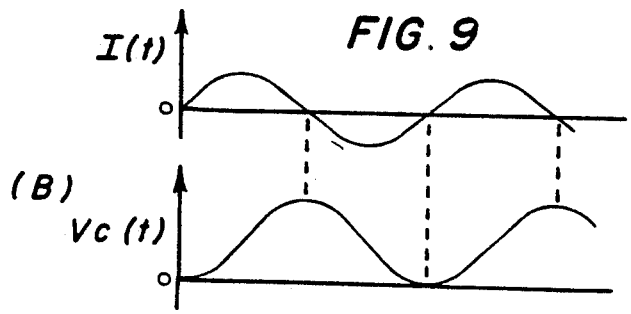
FIG. 9 is a composite graph similar to FIG. 8 showing a second case where the current is applied at its zero point and a capacitor voltage and consequently the electrode voltage has acquired a dc offset.

FIG. 6 shows a current source circuit of interest which has two low frequency poles within a feedback loop. These high-pass circuits prevent the system from acting like a dc current source but unfortunately may cause a finite settling time when a circuit is suddenly energized. The circuit of FIG. 7 can be simplified to the high-frequency equivalent to the circuit of FIG. 7 that is at rest until the current source suddenly begins at some point in its cycle. Since $V_c = 1/C \int idt$, some possibilities for the first few cycles are shown in FIG. 8 and FIG. 9. Note that for the second case shown in FIG. 9, the value of Vc has acquired a dc offset voltage. The offset slowly decreases through R, assuming that the current source approaches a V source at low frequency.

The size of the transient, is easily found to be I/2wc. For 5 mA, 1 micro F and 12.5 kHz, it is 90 mV. To avoid this problem it is necessary to do two things. First the current must be started at its + or − peak. Second the current source must end at the same peak. To change the current source to a new value, the change should be made at the peak point.

Figure 10:
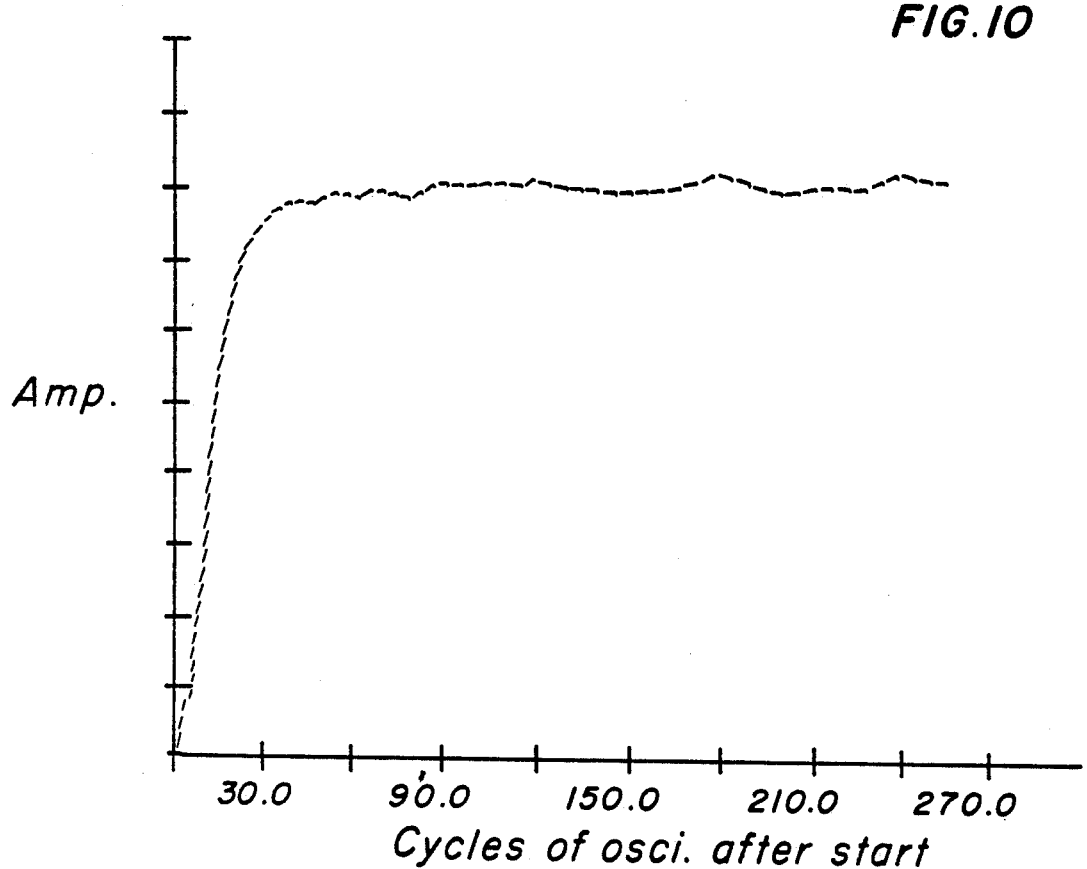
FIG. 10 is a graph plotting the measured voltage at an electrode in relative units against the number of cycles of oscillation of the generator when the current generator is turned on at the zero crossing, corresponding to a worst case possibility according to the present invention.
Figure 11:
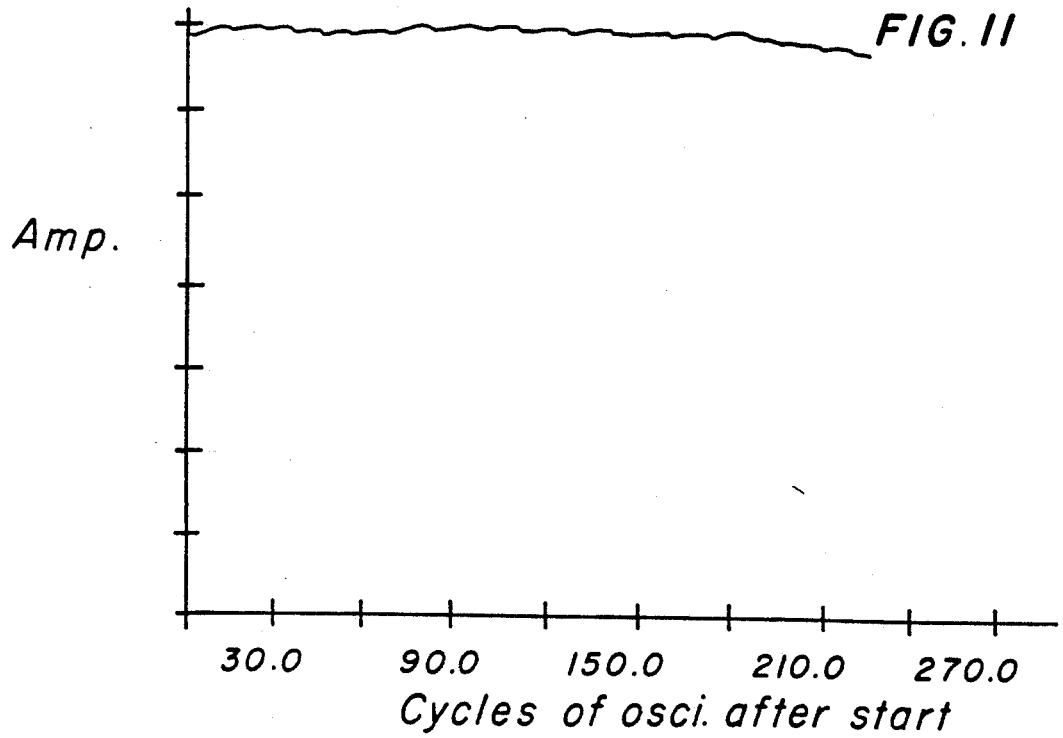
FIG. 11 is a view similar to FIG. 10 showing the results when the current generator is turned on at a peak current value.

In order to test the effectiveness of switching on the current generator at the peak current value, the inventors applied a pair of electrodes to the skin and turned on the current generator at different times in the current generator cycle. Amplitude of the measured voltage was then plotted for each number of cycles of oscillation, beginning when the oscillator was turned on. FIG. 10 and FIG. 11 show the size of the signal obtained during the first 250 cycles of the oscillator. FIG. 10 illustrates the results when the current generator was turned on at the 0 crossing (worst possible time). A steady state amplitude was obtained only after approximately 100 cycles of the oscillator had elapsed. FIG. 11 showed the result of a similar experiment but with a current generator turned on at the optimal instant when the current amplitude was at maximum. With FIGS. 10 and 11 shown on the same scale, it can be seen that except for fluctuations due to noise, the current amplitude was at maximum from the first cycle.

Accordingly the inventors have demonstrated that simple discrete value ac currents can be used in patterns to produce complex images and that system response can be drastically improved by carefully controlling the current generators to apply current only at the instant of peak current values.

To better understand the invention, reference is again made to U.S. Pat. No. 4,920,490. The sequence of operations used in the system disclosed in U.S. Pat. No. 4,920,490 is as follows: As a clocked counter advances, its decoded output consecutively addresses each of the 32 current generators or DAC attenuators 42 in turn. At each address, the DAC receives a particular predetermined digital word from the computer which sets the value and polarity of the current to the electrode. (Each DAC attenuator drives a voltage-to-current converter which is therefore sometimes called a current generator 42). Since all the DAC attenuators are driven from the oscillator which operates at the fairly high frequency of 12.5 kHz, the currents to the electrodes are all 12.5 kHz and sinusoidal and in phase with each other, and they continue to flow until the next time a set of currents is applied. They are carefully adjusted so that the sum of all the positive currents is as nearly equal as possible to all the negative (reversed polarity) currents, so that the net total current in all of the electrodes is as close to zero as possible.

A particular set of currents as described above is termed a pattern in the present application. A typical pattern is a spatial cosine, with the maximum positive current on electrode 1, slightly less on electrode 2, about 71% of maximum on electrode 4, no current on electrode 8, increasing negative currents on electrodes 9 through 16, then decreasing negative currents on electrodes 17 through 24, which has about zero, then increasing currents through electrode 32. The variation of the current in any electrode with time is here termed a waveform. Other patterns are cosines of higher spatial frequency, which go from maximum to zero to negative maximum to zero and back to positive maximum, more than once as one goes from electrode 1 to 32. The highest spatial frequency pattern has alternate electrodes at maximum positive and maximum negative currents. For the present invention all of the sinusoidal patterns of spatial frequency 1 through 31 are usually used to make a single image. After the currents are applied to the electrodes, the electrode voltages must be measured. The invention has a multiplexed system in which a single ADC (analog-to-digital converter) consecutively converts the voltage at each of the 32 electrodes to a digital word which is sent to the computer memory. The same address generator is used to poll the electrode voltages as was used to address the DAC attenuators. After the voltages for the first pattern are read, the second set of currents (spatial pattern) is applied. As each new value is latched into a DAC, the current to its associated electrode changes from the previous to the new value. The data needed for one image is 32 voltage values for each of 31 spatial patterns, or nearly a thousand numbers.

The present invention involves three departures from the mode of operation just described. The first and simplest of these is that a series switch or its equivalent disconnects the oscillator from the points that would energize the current generators. This allows one to apply current flow to all electrodes simultaneously (and turns them off simultaneously) thus avoiding the problem of possible sensation by the subject as the currents are consecutively changed every time a new current pattern is applied. Also the total time that currents are applied to a subject is reduced.

The second improvement is one which can be accomplished by the same series switch, but only by paying special attention to the time at which it is connected and disconnected, which should be at a peak current value, and it should be connected for a finite number of cycles (if closed at the plus peak, it should be opened at a plus peak and, same for minus peaks). Although FIG. 3 shows a single voltmeter multiplexed to read all electrodes consecutively, it is in fact important to implement a separate voltmeter for each electrode in order to increase the overall speed of operation sufficiently. This makes it especially important to avoid voltage transients. It is interesting to note that while the fact that current source connection and disconnection at the peak point will prevent voltage transients is based on elementary circuit theory, the fact that it is true is not very well known and not at all obvious, since the obvious point at which to switch is the current waveform zero crossing, not the peak.

The third improvement of the invention is related to the nature of the spatial current patterns used. In order to use sinusoidal patterns it is necessary to be able to control the current to each electrode so that it can be set to any value between the maximum value and the same maximum value with inverted polarity. To do this requires a "four quadrant" DAC attenuator circuit for each electrode, which is tricky to adjust and relatively expensive. The present invention shows that the spatial current patterns need not be sinusoidal, but that a set of Walsh function type patterns is satisfactory. This means that every current source is always driven by either the maximum value or the same maximum value with inverted polarity. The old requirement that the sum of all the positive currents should equal the sum of the negative currents is still present. In order to implement this, instead of DACs, the invention uses the oscillator signal and its equal value opposite polarity signal. Each channel now has a switch to drive the current generator which supplies one or the other of those signals. The switch is driven by a latch so that it remains in the position set until commanded otherwise. The hardware is clearly simpler and easier to keep in adjustment, but the procedure is just the same as was discussed earlier with the exception that the currents may have only one magnitude and two polarities, and the current patterns used are 31 square waves of different spatial frequencies rather than 31 sinusoids. Note that the 31st spatial frequency is the same for either the sinusoidal or square wave current pattern.

The first improvement can be used without the second, but not vice-versa. The third improvement can be used with or without the first or second.

It should also be clear that while the invention uses a system in which currents are applied to the electrodes and voltages from the electrodes to a common ground measured, a system could be constructed in which voltages are applied to the electrodes and the current to each is measured.

It should also be noted that while a system with sinusoidal currents has been described, systems where the currents applied to the electrodes may be other than sinusoidal should also be feasible. For instance, impedance tomography systems used for materials testing are usually designed for current sources which are very low frequency square waves.

In a similar way, while the discussion has been almost entirely in terms of an ability to reconstruct an image of the variation in resistance (the real part of the impedance) at different points within a body, the invention is actually able to reconstruct the imaginary or reactive components also, and also to reconstruct an image of the total impedance.

While specific embodiments of the invention have been shown and described in detail to illustrate the application of the principles of the invention, it will be understood that the invention may be embodied otherwise without departing from such principles.

What is claimed is:

1. An electrical impedance imaging method using means for forming images of internal impedances at a multiplicity of points within a body and temporal variations of the impedances using an array of electrodes on the surface of the body, a plurality of current generators, each for applying a current to a respective single electrode, means for generating a plurality of current patterns and means for measuring a voltage at each electrode for each current pattern, the improvement comprising:
   controlling each current generator for generating ac currents, the current of all the generators together forming current patterns with differing spatial frequencies;
   applying and removing the currents of each current pattern to and from all the current generators respectively to and from all the electrodes simultaneously;
   measuring the voltage at each electrode; and
   providing the measured voltage at each electrode to the means for forming images.

2. A method according to claim 1, including controlling each current generator so that the currents are in waveforms having simultaneous plus peak and minus peak values, the method including initially applying each current waveform to a respective electrode at the instant when the current waveform is at a peak value.

3. A method according to claim 2, including controlling each current generator to discontinue the application of the current waveform when the current waveform is at a peak value corresponding to the peak value at which the current waveform was applied.

4. A method according to claim 2, wherein all nonzero currents of a current pattern have the same magnitude for all electrodes, with the magnitude having positive polarity for approximately one half of the electrodes and negative polarity for a remainder of the electrodes.

5. A method according to claim 1, wherein all nonzero currents of a current pattern have the same magnitude for all electrodes, with the magnitude having positive polarity for approximately one half of the electrodes and negative polarity for a remainder of the electrodes.

* * * * *